(12) United States Patent
Guha et al.

(10) Patent No.: US 8,889,728 B2
(45) Date of Patent: Nov. 18, 2014

(54) STABLE PHARMACEUTICAL COMPOSITIONS OF CARVEDILOL

(75) Inventors: Ashish Guha, Pune (IN); Bharat Metkar, Pune (IN); Makrand Krishnakumar Avachat, Pune (IN)

(73) Assignee: Lupin Limited, Mumbai, Maharashtra (IN)

( * ) Notice: Subject to any disclaimer, the term of this patent is extended or adjusted under 35 U.S.C. 154(b) by 719 days.

(21) Appl. No.: 12/921,261

(22) PCT Filed: Mar. 4, 2009

(86) PCT No.: PCT/IN2009/000147
§ 371 (c)(1),
(2), (4) Date: Sep. 7, 2010

(87) PCT Pub. No.: WO2009/110004
PCT Pub. Date: Sep. 11, 2009

(65) Prior Publication Data
US 2011/0005960 A1    Jan. 13, 2011

(30) Foreign Application Priority Data
Mar. 4, 2008 (IN) .............................. 419/KOL/2008

(51) Int. Cl.
*A61K 31/403* (2006.01)
*B65D 81/26* (2006.01)
*A61K 9/50* (2006.01)

(52) U.S. Cl.
CPC ............. *A61K 31/403* (2013.01); *A61K 9/5078* (2013.01)
USPC ............ 514/411; 206/204; 206/528; 424/451

(58) Field of Classification Search
USPC ......... 206/204, 528–540, 570–572; 424/76.1, 424/600, 400, 451, 455, 462; 514/207, 411
See application file for complete search history.

(56) References Cited

U.S. PATENT DOCUMENTS

| 3,826,358 | A | * | 7/1974 | Butler et al. ................... | 206/204 |
|---|---|---|---|---|---|
| 4,503,067 | A | | 3/1985 | Wiedemann et al. | |
| 5,018,621 | A | * | 5/1991 | O'Connell, Jr. ............... | 206/204 |
| 5,114,003 | A | * | 5/1992 | Jackisch et al. ............... | 206/204 |
| 6,571,942 | B2 | * | 6/2003 | Riemenschneider et al. .............................. | 206/204 |
| 7,413,083 | B2 | * | 8/2008 | Belfance et al. .............. | 206/540 |
| 7,871,558 | B2 | * | 1/2011 | Merical et al. ................ | 264/539 |
| 8,110,260 | B2 | * | 2/2012 | Merical et al. ................ | 206/204 |
| 2004/0019096 | A1 | | 1/2004 | Andronis et al. | |
| 2004/0204474 | A1 | * | 10/2004 | Decker et al. ................. | 514/411 |
| 2004/0234602 | A1 | | 11/2004 | Fischer et al. | |
| 2005/0261335 | A1 | | 11/2005 | Chen et al. | |
| 2005/0271721 | A1 | | 12/2005 | Gabel et al. | |
| 2009/0263478 | A1 | * | 10/2009 | Arnold et al. ................. | 514/411 |
| 2012/0039949 | A1 | * | 2/2012 | Fretzen et al. ................ | 424/400 |

FOREIGN PATENT DOCUMENTS

WO    WO 99/52526    10/1999

OTHER PUBLICATIONS

PCT/IN2009/000147 International Preliminary Report on Patentability and Written Opinion of the International Searching Authority, issued Sep. 7, 2010, 7 pages.

* cited by examiner

*Primary Examiner* — Luan K Bui
(74) *Attorney, Agent, or Firm* — Fulbright & Jaworski L.L.P.

(57) ABSTRACT

A stable solid oral pharmaceutical composition comprising carvedilol or a pharmaceutically acceptable salt thereof, which is packed using a suitable packaging material along with a desiccant. A process for manufacturing a stable solid oral dosage form containing carvedilol or a pharmaceutically acceptable salt thereof, which is packed in the packaging configuration comprising moisture permeation inhibitory packaging. A method of preparing a stable solid oral pharmaceutical dosage form, said method comprising, encasing a pharmaceutical dosage form comprising carvedilol or pharmaceutically acceptable salt thereof in a container comprising a desiccant. A pharmaceutical kit comprising a container impervious to moisture, wherein said container comprises a desiccant; and a solid oral pharmaceutical dosage form comprising carvedilol or a pharmaceutically acceptable salt thereof, wherein said pharmaceutical dosage form is encased in said container.

10 Claims, No Drawings

STABLE PHARMACEUTICAL COMPOSITIONS OF CARVEDILOL

CROSS-REFERENCE TO RELATED APPLICATIONS

This application is a Section 371 National Stage Application of International No. PCT/IN2009/000147, filed Mar. 4, 2009 and published as WO 2009/110004 A1 on Sept. 11, 2009, which claims priority from the India Application 419/KOL/2008, filed Mar. 4, 2008, the contents of which are incorporated herein in their entirety for all purposes.

FIELD OF THE INVENTION

The present invention relates to stable solid oral pharmaceutical compositions of carvedilol or a pharmaceutically acceptable salt thereof.

BACKGROUND OF THE INVENTION

U.S. Pat. No. 4,503,067 describes a compound, which is known as carvedilol. This compound is a novel multiple action drug useful in the treatment of mild to moderate hypertension. Carvedilol is known to be both a competitive non-selective β-adrenoceptor antagonist and a vasodilator. The vasodilatory actions of carvedilol result primarily from $\alpha_1$-adrenoceptor blockade, whereas the β-adrenoceptor blocking activity of the drug prevents reflex tachycardia when used in the treatment of hypertension. These multiple actions of carvedilol are responsible for the antihypertensive efficacy of the drug. Also, carvedilol, as a consequence of its antioxidant action in attenuating oxygen free radical-initiated lipid peroxidation, is useful in organ protection, in particular, cardio protection. Additionally, carvedilol is useful in the treatment of congestive heart failure.

US patent application 2004/0234602 discloses use of stabilizing agents like antioxidants suitable for use also in situation where the active substance is subject to oxidation: acids (ascorbic acid, erythorbic acid, etidronic acid, gallic acid, hypophosphorous acid, nordihydroguairetic acid, propionic acid etc.), phenols (e.g. BHA, BHT, t-butyl hydroquinone, dodecyl gallate, octyl gallate, 1,3,5-trihydroxybenzene), organic and inorganic salts (calcium ascorbate, sodium ascorbate, sodium bisulphite, sodium metabisulfite, sodium sulfite, potassium bisulphite, potassium metabisulphite), esters (calcium ascorbate, dilauryl thiodipropionate, dimyristyl thiodipropionate, distearyl thiodipropionate), pyranon (maltol), and vitamin E (tocopherol, D-α-tocopherol, DL-α-tocopherol, tocopheryl acetate, d-α-tocopheryl acetate, dl-α-tocopheryl acetate.

A need exists in the art for methods to stabilize solid oral pharmaceutical dosage forms comprising carvedilol or a pharmaceutically acceptable salts thereof. These stabilized pharmaceutical dosage forms would allow for longer storage periods, and would allow the amount of components to remain constant over the storage period.

BRIEF SUMMARY OF THE INVENTION

An object of the invention is to provide stable solid pharmaceutical compositions for oral administration comprising carvedilol or a pharmaceutically acceptable salt thereof.

It is an object of the invention to provide a process for manufacturing a stable solid oral dosage form containing carvedilol or a pharmaceutically acceptable salt thereof, which is packed in the packaging configuration comprising moisture permeation inhibitory packaging.

It is an object of the invention to provide a method of preparing a pharmaceutical dosage form, the method comprising encasing a pharmaceutical dosage form comprising carvedilol or a pharmaceutically acceptable salt thereof in a container essentially impervious to moisture and comprising a desiccant.

It is an object of the invention to provide a pharmaceutical kit, the pharmaceutical kit comprising (a) a container impervious to moisture, wherein the container contains a desiccant, and (b) a pharmaceutical dosage form comprising carvedilol or a pharmaceutically acceptable salts thereof, wherein the pharmaceutical dosage form is encased in the container.

DETAILED DESCRIPTION OF THE INVENTION

The present invention relates to stable solid oral pharmaceutical compositions of carvedilol or a pharmaceutically acceptable salt thereof.

Carvedilol or a pharmaceutically acceptable salt thereof is preferably carvedilol phosphate. Carvedilol phosphate is either amorphous or crystalline in nature or mixture thereof.

Stabilization in a package form is provided in order to improve the stability of the solid dosage form of the present invention at storage or transportation. The stabilization of the solid dosage form containing carvedilol or a pharmaceutically acceptable salt thereof, compound of the present invention can be improved by using package form such as package suppressing the permeation of moisture.

Suitable packaging material comprises a high-density polyethylene (HDPE) container.

The container can additionally contain a desiccant. A desiccant is any drying agent that removes moisture from the air. Desiccants include, but are not limited to, silica gel, clay desiccants, calcium sulfate, calcium chloride, calcium oxide, zeolite, activated alumina, activated charcoal and combinations thereof.

The moisture permeation inhibitory packaging is material is preferably hydroxypropylmethylcellulose (HPMC) based capsule.

The stable solid oral pharmaceutical compositions of the present invention are those known to a person ordinarily skilled in the art. These may comprises of pellets, beads, granules, spheroids, mini tablets and capsules. The stable solid oral pharmaceutical composition of the present invention is a sustained release, controlled release, extended release, modified release, pulsed release, immediate release dosage form or combination thereof.

Controlled release compositions of carvedilol phosphate are prepared and tested for related substances by storing in HDPE container with desiccant and without desiccant.

EXAMPLES

Example 1

Controlled Release Composition of Carvedilol Phosphate

| Stage I: Drug Loading | | |
|---|---|---|
| S. No. | Name of Ingredient | Quantity (mg) |
| 1 | Carvedilol Phosphate | 8.0 |
| 2 | Sugar Spheres NF | 190.00 |
| 3 | Hydroxypropylmethylcellulose | 2.6 |
| 4 | Dichloromethane | Q.S. |
| 5 | Methanol | Q.S. |

Prepare a solution of hydroxypropylmethylcellulose & carvedilol phosphate in methanol and dichloromethane. This solution is sprayed onto sugar spheres.

Stage II: Extended Release Coating

| S. No. | Name of Ingredient | Quantity (mg) |
| --- | --- | --- |
| 1 | Stage I pellets | |
| 2 | Ethyl cellulose | 10.0 |
| 3 | Hydroxypropylmethylcellulose | 15.0 |
| 4 | Triethyl citrate | 2.5 |
| 5 | Dichloromethane | Q.S. |
| 6 | Isopropyl Alcohol | Q.S. |

Prepare a solution of ethyl cellulose and hydroxypropylmethylcellulose in isopropyl alcohol, dichloromethane and triethyl citrate. Spray this solution onto pellets of stage I.

Stage III: Immediate Release Drug Loading

| S. No. | Name of Ingredient | Quantity (mg) |
| --- | --- | --- |
| 1 | Stage II pellets | |
| 2 | Carvedilol Phosphate | 18.0 |
| 3 | Hydroxypropylmethylcellulose | 5.8 |
| 4 | Dichloromethane | Q.S. |
| 5 | Methanol | Q.S. |

Prepare a solution of carvedilol phosphate, hydroxypropylmethylcellulose in dichloromethane and methanol. Spray this solution onto pellets of stage II.

Stage IV: Enteric Coating

| S. No. | Name of Ingredient | Quantity (mg) |
| --- | --- | --- |
| 1 | Stage III pellets | |
| 2 | Hydroxypropylmethylcellulose phthalate | 39.2 |
| 3 | Triethyl citrate | 3.9 |
| 4 | Dichloromethane | Q.S. |
| 5 | Isopropyl Alcohol | Q.S. |

Prepare a solution of hydroxypropylmethylcellulose phthalate in dichloromethane and isopropyl alcohol. Add triethyl citrate and spray this solution onto pellets of stage III.

Stage V: Immediate Release Drug Loading

| S. No. | Name of Ingredient | Quantity (mg) |
| --- | --- | --- |
| 1 | Stage IV pellets | |
| 2 | Carvedilol Phosphate | 14.0 |
| 3 | Hydroxypropylmethylcellulose | 4.5 |
| 4 | Dichloromethane | Q.S. |
| 5 | Methanol | Q.S. |

Prepare a solution of carvedilol phosphate and hydroxypropylmethylcellulose in dichloromethane and methanol. Spray this solution onto pellets of stage IV.

Stage VI: Protective Coating

| S. No. | Name of Ingredient | Quantity (mg) |
| --- | --- | --- |
| 1 | Stage V pellets | |
| 2 | Hydroxypropylmethylcellulose | 17.9 |
| 3 | Dichloromethane | Q.S. |
| 4 | Isopropyl Alcohol | Q.S. |

Prepare a solution of hydroxypropylmethylcellulose in dichloromethane and isopropyl alcohol. Spray this solution onto pellets of stage V.

Carry out the assay of pellets to calculate the fill weight. Based on 100% assay, these pellets are filled into hard gelatin capsules.

Example 2

Controlled Release Composition of Carvedilol Phosphate

Stage I: Drug Loading

| S. No. | Name of Ingredient | Quantity (mg) |
| --- | --- | --- |
| 1 | Carvedilol Phosphate | 80.0 |
| 2 | Sugar Spheres NF | 200.0 |
| 3 | Povidone | 20.0 |
| 4 | Talc | 20 |
| 5 | Methanol | Q.S. |

Dissolve povidone and carvedilol phosphate in methanol. Talc is dispersed in it. Spray this solution onto sugar spheres.

Stage II: Barrier Coating

| S. No. | Name of Ingredient | Quantity (mg) |
| --- | --- | --- |
| 1 | Stage I pellets | |
| 2 | Hydroxypropylmethylcellulose | 16.25 |
| 3 | Triethyl citrate | 1.63 |
| 4 | Methanol | Q.S. |

Prepare a solution of hydroxypropylmethylcellulose in methanol. Add triethyl citrate and spray this solution onto pellets of stage I.

Stage III: Enteric Coating

| S. No. | Name of Ingredient | Quantity (mg) |
| --- | --- | --- |
| 1 | Stage II pellets | |
| 2 | Eudragit | 24.0 |
| 3 | Hydroxypropylmethylcellulose | 10.29 |
| 4 | Triethyl citrate | 3.43 |
| 5 | Talc | 24.0 |
| 6 | Isoproply Alcohol | Q.S. |
| 7 | Dichloromethane | Q.S. |

Disperse eudragit in dichloromethane. Disperse hydroxypropylmethylcellulose in isopropyl alcohol. These two dispersions are mixed to get a clear solution. Add triethyl citrate and sprayed onto pellets of stage II.

Carry out the assay of pellets to calculate the fill weight. Based on 100% assay, these pellets are filled into hard gelatin capsules.

Example 3

Controlled Release Compositions of Carvedilol Phosphate

Stage I: Drug Loading

| S. No. | Name of Ingredient | Quantity (mg) |
| --- | --- | --- |
| 1 | Carvedilol Phosphate | 64.0 |
| 2 | Sugar Spheres NF | 172.00 |
| 3 | Povidone | 16.0 |
| 4 | Talc | 16.0 |
| 5 | Methanol | Q.S. |

Dissolve povidone & carvedilol phosphate in methanol and talc is dispersed in it. This solution is sprayed onto sugar spheres.

Stage II: Barrier Coating

| S. No. | Name of Ingredient | Quantity (mg) |
| --- | --- | --- |
| 1 | Stage I pellets | |
| 2 | Hydroxypropylmethylcellulose | 13.6 |
| 3 | Triethyl citrate | 1.4 |
| 4 | Methanol | Q.S. |

Prepare a solution of Hydroxypropylmethylcellulose in methanol. Add tirethyl citrate to this solution and sprayed onto the pellets of stage I.

Stage III: Enteric Coating

| S. No. | Name of Ingredient | Quantity (mg) |
| --- | --- | --- |
| 1 | Stage II pellets | |
| 2 | Eudragit | 20.09 |
| 3 | Hydroxypropylmethylcellulose | 8.61 |
| 4 | Triethyl citrate | 2.87 |
| 5 | Talc | 20.09 |
| 6 | Dichloromethane | Q.S. |
| 7 | Isopropyl Alcohol | Q.S. |

Disperse Hydroxypropylmethylcellulose in isopropyl alcohol. Separately, disperse eudragit in dichloromethane. Add these two dispersions and stirred to get a clear solution. Add tirethyl citrate and talc. Spray this solution onto the pellets of stage II.

Stage IV: Barrier Coating

| S. No. | Name of Ingredient | Quantity (mg) |
| --- | --- | --- |
| 1 | Stage III pellets | |
| 2 | Hydroxypropylmethylcellulose | 16.93 |
| 3 | Triethyl citrate | 1.69 |
| 4 | Dichloromethane | Q.S. |
| 5 | Isopropyl Alcohol | Q.S. |

Prepare a solution of Hydroxypropylmethylcellulose in isopropyl alcohol. Add triethyl citrate to dichloromethane. Add these solutions and sprayed onto the pellets of stage III.

Stage V: Immediate Release Drug Loading

| S. No. | Name of Ingredient | Quantity (mg) |
| --- | --- | --- |
| 1 | Stage IV pellets | |
| 2 | Carvedilol Phosphate | 16.0 |
| 3 | Povidone | 4.0 |
| 4 | Talc | 4.0 |
| 5 | Methanol | Q.S. |

Dissolve povidone and carvedilol phosphate in methanol. Disperse talc in it and sprayed onto pellets of stage IV.

Stage VI: Protective Coating

| S. No. | Name of Ingredient | Quantity (mg) |
| --- | --- | --- |
| 1 | Stage V pellets | |
| 2 | Hydroxypropylmethylcellulose | 19.11 |
| 3 | Triethyl citrate | 1.91 |
| 4 | Methanol | Q.S. |

Dissolve Hydroxypropylmethylcellulose in methanol. Add triethyl citrate and spray this solution onto pellets of stage V.

Carry out the assay of pellets to calculate the fill weight. Based on 100% assay, these pellets are filled into hydroxpropylmethylcellulose-based capsules.

Extended release compositions of carvedilol phosphate are subjected to stability studies at 40° C.±2° C. & 75±5% relative humidity and tested for related substances by storing in HDPE containers with and without desiccant and the results are enumerated in Tables 1-6.

TABLE 1

Stability Study of Example 1 by storing in HDPE container without Desiccant for Related Substances Study (40° C. ± 2° C. & 75 ± 5% RH)

| Related Substance | Initial | 2 month |
| --- | --- | --- |
| Impurity A | BDL | BDL |
| Impurity B | 0.040 | 0.060 |
| Impurity C | 0.027 | 0.049 |
| Impurity D | BDL | 0.111 |
| Impurity E | BDL | BDL |
| Unknown | 0.038 | 0.370 |
| Total Impurity | 0.105 | 0.697 |

TABLE 2

Stability Study of Example 1 by storing in HDPE container with 1 g silica as desiccant for Related Substances Study (40° C. ± 2° C. & 75 ± 5% RH)

| Related Substance | Initial | 2 month |
| --- | --- | --- |
| Impurity A | BDL | BDL |
| Impurity B | 0.040 | 0.061 |
| Impurity C | 0.027 | 0.034 |
| Impurity D | BDL | 0.035 |
| Impurity E | BDL | BDL |
| Unknown | 0.038 | 0.063 |
| Total Impurity | 0.105 | 0.240 |

TABLE 3

Stability Study of Example 2 by storing in HDPE container without Desiccant for Related Substances Study (40° C. ± 2° C. & 75 ± 5% RH)

| Related Substance | Initial | 1 month |
|---|---|---|
| Impurity A | 0.060 | 0.079 |
| Impurity B | 0.012 | 0.011 |
| Impurity C | 0.033 | 0.078 |
| Impurity D | 0.002 | 0.002 |
| Impurity E | BDL | BDL |
| Unknown | 0.025 | 0.048 |
| Total Impurity | 0.167 | 0.345 |

TABLE 4

Stability Study of Example 2 by storing in HDPE container with 1 g silica as desiccant for Related Substances Study (40° C. ± 2° C. & 75 ± 5% RH)

| Related Substance | Initial | 1 month |
|---|---|---|
| Impurity A | 0.060 | 0.067 |
| Impurity B | 0.012 | 0.013 |
| Impurity C | 0.033 | 0.073 |
| Impurity D | 0.002 | 0.002 |
| Impurity E | BDL | BDL |
| Unknown | 0.025 | 0.041 |
| Total Impurity | 0.167 | 0.276 |

TABLE 5

Stability Study of Example 3 by storing in HDPE container without Desiccant for Related Substances Study (40° C. ± 2° C. & 75 ± 5% RH)

| Related Substance | Initial | 1 month |
|---|---|---|
| Impurity A | BDL | 0.112 |
| Impurity B | 0.010 | 0.016 |
| Impurity C | BDL | BDL |
| Impurity D | BDL | BDL |
| Impurity E | BDL | BDL |
| Unknown | 0.045 | 0.075 |
| Total Impurity | 0.084 | 0.254 |

TABLE 6

Stability Study of Example 3 by storing in HDPE container with 1 g silica as desiccant for Related Substances Study (40° C. ± 2° C. & 75 ± 5% RH)

| Related Substance | Initial | 1 month |
|---|---|---|
| Impurity A | BDL | 0.094 |
| Impurity B | 0.010 | 0.014 |
| Impurity C | BDL | BDL |
| Impurity D | BDL | BDL |
| Impurity E | BDL | BDL |
| Unknown | 0.045 | 0.054 |
| Total Impurity | 0.084 | 0.191 |

The results from Tables 1-6 reveal that suitable moisture permeation inhibitory packaging materials make the solid oral dosage form of carvedilol phosphate more stable. The total impurity is high when these solid oral dosage forms are packed in a HDPE container without desiccant as compared to a HDPE container with desiccant.

Further, the use of HPMC based capsule having low moisture content of 3-8% as compared to gelatin capsule containing 13-14% moisture makes the solid oral dosage forms of carvedilol phosphate more stable (Tables 5 & 6).

In another embodiment, the present invention also relates to a process for manufacturing a stable solid oral dosage form containing carvedilol or a pharmaceutically acceptable salt thereof, which is packed in the packaging configuration comprising moisture permeation inhibitory packaging.

In another embodiment, the present invention also relates to a method of preparing a stable solid oral pharmaceutical dosage form, said method comprising, encasing a pharmaceutical dosage form comprising carvedilol or pharmaceutically acceptable salt thereof in a container comprising a desiccant.

In another embodiment, the present invention also relates to a pharmaceutical kit comprising: (a) a container impervious to moisture, wherein said container comprises a desiccant; and (b) a solid oral pharmaceutical dosage form comprising carvedilol or a pharmaceutically acceptable salt thereof, wherein said pharmaceutical dosage form is encased in said container.

The invention claimed is:

1. A stable solid oral pharmaceutical composition comprising carvedilol phosphate filled into a hydroxypropylmethylcellulose-based capsule, which is packed in a container using a suitable packaging material along with a desiccant, wherein the composition is more stable compared to the carvedilol phosphate composition filled in a gelatin capsule.

2. A stable solid oral pharmaceutical composition of claim 1, wherein the composition comprises a drug loaded core and one or more outer coatings.

3. A stable solid oral pharmaceutical composition of claim 2, wherein the outer coating comprises an enteric coating and an immediate release coating.

4. A stable solid oral pharmaceutical composition of claim 2, wherein carvedilol phosphate is amorphous.

5. The stable solid oral pharmaceutical compositions of claim 1, wherein the suitable packaging material is a high-density polyethylene container.

6. The stable solid oral pharmaceutical compositions of claim 1, wherein the desiccant is selected from the group comprising silica gel, molecular sieve, clay desiccants, calcium sulfate, calcium chloride, calcium oxide, zeolite, activated alumina, activated charcoal and combinations thereof.

7. The stable solid oral pharmaceutical compositions of claim 2, wherein
 a. the drug loaded core comprising carvedilol phosphate:,
 b. a first barrier coating surrounding the drug loaded core;
 c. an enteric coating over the first barrier coating of (b);
 d. a second barrier coating over the enteric coating of (c);
 e. an immediate release coating comprising carvedilol phosphate (d);
 f. a protective coating over the immediate release coating of (e).

8. The stable solid oral pharmaceutical composition of claim 1, is a sustained release, controlled release, extended release, modified release, pulsed release, immediate release dosage form or combination thereof.

9. The method of preparing the hydroxypropylmethylcellulose-based capsule of claim 1, wherein the method comprising, encasing the hydroxypropylmethylcellulose-based capsule comprising the carvedilol phosphate in the container comprising the desiccant.

10. A pharmaceutical kit comprising: (a) a container impervious to moisture, wherein said container comprises a desiccant; and (b) a solid oral pharmaceutical dosage form comprising carvedilol phosphate filled into a hydroxypropylmethylcellulose-based capsule, wherein said pharmaceutical dosage form is encased in said container, wherein the composition is more stable compared to the carvedilol phosphate filled in a gelatin capsule.

* * * * *